(12) United States Patent
Abe

(10) Patent No.: US 11,685,902 B2
(45) Date of Patent: Jun. 27, 2023

(54) PRODUCTION METHOD FOR KIDNEY-LIKE TISSUE

(71) Applicant: Tokushima University, Tokushima (JP)

(72) Inventor: Hideharu Abe, Tokushima (JP)

(73) Assignee: TOKUSHIMA UNIVERSITY, Tokushima (JP)

(*) Notice: Subject to any disclaimer, the term of this patent is extended or adjusted under 35 U.S.C. 154(b) by 955 days.

(21) Appl. No.: 16/341,175

(22) PCT Filed: Oct. 6, 2017

(86) PCT No.: PCT/JP2017/036413
§ 371 (c)(1),
(2) Date: Apr. 11, 2019

(87) PCT Pub. No.: WO2018/070346
PCT Pub. Date: Apr. 19, 2018

(65) Prior Publication Data
US 2020/0181579 A1    Jun. 11, 2020

(30) Foreign Application Priority Data

Oct. 11, 2016    (JP) ................ 2016-199952

(51) Int. Cl.
*C12N 5/071*    (2010.01)
*G01N 33/50*    (2006.01)

(52) U.S. Cl.
CPC ....... *C12N 5/0686* (2013.01); *G01N 33/5044* (2013.01); *C12N 2502/02* (2013.01); *C12N 2502/1352* (2013.01); *C12N 2502/28* (2013.01); *C12N 2503/04* (2013.01)

(58) Field of Classification Search
None
See application file for complete search history.

(56) References Cited

U.S. PATENT DOCUMENTS

| | | | |
|---|---|---|---|
| 2009/0060961 A1* | 3/2009 | Naruse | C08J 9/36 428/401 |
| 2011/0045500 A1 | 2/2011 | Taniguchi et al. | |
| 2011/0217725 A1 | 9/2011 | Itchoda et al. | |
| 2016/0137985 A1 | 5/2016 | Osafune et al. | |
| 2016/0177270 A1 | 6/2016 | Takebe et al. | |
| 2017/0067014 A1 | 3/2017 | Takebe et al. | |

FOREIGN PATENT DOCUMENTS

| | | |
|---|---|---|
| JP | 2015-510500 A | 4/2015 |
| JP | 2015-529523 A | 10/2015 |
| WO | WO-2009/099152 A1 | 8/2009 |
| WO | WO-2010/047132 A1 | 4/2010 |

(Continued)

OTHER PUBLICATIONS

Wikipedia, https://en.wikipedia.org/wiki/HEK_293_cells, accessed Apr. 22, 2022.*

(Continued)

*Primary Examiner* — Erin M. Bowers
(74) *Attorney, Agent, or Firm* — Cesari & McKenna, LLP

(57) ABSTRACT

A novel tissue usable for a kidney tissue model is provided. A method for producing a kidney-like tissue includes co-culturing a cell group containing mesenchymal stem cells, vascular endothelial cells, and clonal embryonic kidney cells.

14 Claims, 12 Drawing Sheets
Specification includes a Sequence Listing.

(56) References Cited

FOREIGN PATENT DOCUMENTS

| WO | WO-2013/103811 A2 | 7/2013 |
|----|-------------------|--------|
| WO | WO-2014/039427 A1 | 3/2014 |
| WO | WO-2014/200115 A1 | 12/2014 |
| WO | WO-2015/012158 A1 | 1/2015 |
| WO | WO-2015/129822 A1 | 9/2015 |

OTHER PUBLICATIONS

Ren et al., Biochem. Biophys. Res. Comm. 338: 1818-1824 (2005).*

Takasato et al "Kidney organoids from human iPS cells contain multiple lineages and model human nephrogenesis"; Nature, 2015, pp. 564-568, vol. 526.

Morizane et al "Nephron organoids derived from human pluripotent stem cells model kidney development and injury"; Nature Biotechnology, 2015, pp. 1193-1200, vol. 33, No. 11.

\* cited by examiner (A)

(B)

(C)

(A)

(B)

(A)

(B)

(C)

(D)

(E)

(F)

PRODUCTION METHOD FOR KIDNEY-LIKE TISSUE

CROSS REFERENCE TO RELATED APPLICATIONS

This application is the National Stage of International Application No. PCT/JP2017/036413, filed on Oct. 6, 2017, which claims priority to Japanese Application No. 2016-199,952, filed on Oct. 11, 2016. The contents of each application are hereby incorporated by reference in their entirety.

TECHNICAL FIELD

A technique concerning a kidney tissue model is disclosed.

BACKGROUND ART

The kidneys in mammals are essential for maintaining the homeostasis of the body by controlling the water-base balance and excreting waste products over the course of life. Renal diseases continue to rise across advanced countries, becoming a serious issue. Glomerular diseases are now considered to be largely responsible for worldwide cost increases associated with end-stage renal disease (ESRD).

A full-sized adult kidney is composed of more than 60 cell species, and has an anatomically complex structure. Due to its complexity and postmitotic nature, podocytes are the most vulnerable component of the glomerular filtration barrier. Unfortunately, little is known about the molecular nature in the repair mechanism in defending podocytes from a range of environmental stresses. Podocytes form a filtration barrier together with capillary endothelial cells and a glomerular basement membrane (GBM), enabling selective permeability of the glomerular capillary wall. Damage to podocytes plays a key role in the progress of glomerular diseases and the development of glomerulosclerosis.

Podocytes are highly specialized cells, and their functions include support for glomerular capillaries, synthesis of a glomerular basement membrane, and regulation of selective glomerular permeability. It has been on the agenda in developmental biology and regenerative medicine to construct nephron progenitor cells that reconstruct a three-dimensional (3D) nephron structure in vitro, and to maintain the cells. The concept of constructing an in vitro 3D tissue-like structure of organs usable as a model system is a fascinating experimental approach.

CITATION LIST

Patent Literature

PTL 1: JP2015-510500
PTL 2: WO2009/099152
PTL 3: WO2010/047132
PTL 4: WO2014/200115

Non-Patent Literature

NPL 1: Takasato et al., Nature, Vol. 526, 564-568, 2015
NPL 2: Morizane et al., Nature Biotechnology, Vol. 33, 1193-1200

SUMMARY OF INVENTION

Technical Problem

In view of the current status of the art, an object is to provide a novel tissue usable as a kidney tissue model.

Solution to Problem

To achieve the object, the inventor conducted extensive research, and found that a self-organized, three-dimensional, kidney-like tissue is formed by co-culturing embryonic kidney cells, mesenchymal stem cells, and vascular endothelial cells; and that the tissue exhibits a gene expression profile equivalent to that of podocytes. The gene expression profile of the tissue was also found to be closer to the gene expression profile of adult kidneys than that of embryonic kidney cells. The inventor conducted further research based on these findings, and found that co-culturing the three types of cells in combination with renal tubular cells and/or mesangial cells provides a three-dimensional kidney-like tissue that even has features of the renal tubular. The inventor conducted further research based on these findings, and the following representative inventions are provided.

Item 1.
A method for producing a kidney-like tissue, the method comprising:
co-culturing a cell group containing a mesenchymal stem cell, a vascular endothelial cell, and a clonal embryonic kidney cell.

Item 2.
The method according to item 1, wherein the
mesenchymal stem cell, the vascular endothelial cell, and the clonal embryonic kidney cell are derived from a human or a mouse.

Item 3.
The method according to item 1 or 2, wherein the clonal embryonic kidney cell is HEK cell or M15 cell.

Item 4.
The method according to item 1 or 2, wherein the cell group is free from iPS cell, ES cell, and a differentiation-induced cell thereof.

Item 5.
The method according to any one of items 1 to 4, wherein the co-culture is performed for 12 hours or more, and 36 hours or less.

Item 6.
The method according to any one of items 1 to 5, wherein the cell count ratio of the mesenchymal stem cell to the clonal embryonic kidney cell (mesenchymal stem cell:clonal embryonic kidney cell) is 1:10 to 10:1.

Item 7.
The method according to any one of items 1 to 6, wherein the cell group further contains a renal tubular cell and/or a mesangial cell.

Item 8.
The method according to any one of items 1 to 7, wherein the kidney cell has an exogenous gene introduced therein.

Item 9.
A kidney-like tissue obtained by the method of any one of items 1 to 8.

Item 10.
Use of the kidney-like tissue of item 9 for a kidney model.

Item 11.

A method for screening for a substance that affects a renal disease, the method comprising:

adding a candidate substance to the kidney-like tissue of item 9, and comparing a gene expression profile of the kidney-like tissue before the addition of the candidate substance with a gene expression profile of the kidney-like tissue after the addition of the candidate substance.

Advantageous Effects of Invention

The present technique saves the trouble of inducing differentiation, and is free from risk of developing cancer, compared with the use of iPS cells. A special medium for induction is also unnecessary, and a typical medium for cell culture can be used. A short-time culture (e.g., 24 hours) can provide a self-organized, kidney-like tissue. A model tissue that exhibits a profile much closer to that of adult kidneys is provided. A kidney tissue model characteristic of an individual, such as a renal disease patient, is also available by preparing the tissue using kidney cells of the individual.

DESCRIPTION OF EMBODIMENTS

Figure 1:
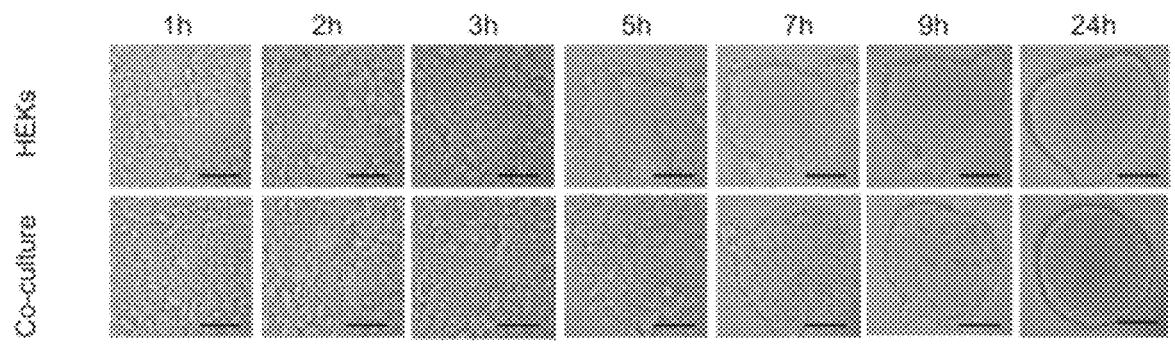
FIG. 1 shows morphological changes over time of cell aggregates obtained by monoculture of human embryonic kidney cells; or by co-culture of endothelial cells, mesenchymal stem cells, and human embryonic kidney cells.

Provided is a method for producing a kidney-like tissue, comprising co-culturing a cell group containing mesenchymal stem cells, vascular endothelial cells, and clonal embryonic kidney cells.

The type of mesenchymal stem cells can be any type, and is not particularly limited as long as kidney-like microspheres can be formed by co-culturing the mesenchymal stem cells together with vascular endothelial cells and clonal embryonic kidney cells. Examples of mesenchymal stem cells include those derived from a tissue selected from the group consisting of bone marrow, adipose tissue, peripheral blood, skin, hair root, muscle tissue, endometrium, placenta, and umbilical cord blood. Mesenchymal stem cells may be derived from a human, or an animal other than humans. Examples of the animal other than humans include mice, rats, dogs, monkeys, swine, chimpanzees, goats, and cows. In an embodiment, the animal is preferably a mouse. In an embodiment, mesenchymal stem cells are preferably those derived from a human. Mesenchymal stem cells isolated from a living body may be used, or commercially available mesenchymal stem cells may also be suitably selected for use.

The type of vascular endothelial cells can be any type, and is not particularly limited, as long as kidney-like microspheres can be formed by co-culturing the vascular endothelial cells together with mesenchymal stem cells and clonal embryonic kidney cells. Examples of vascular endothelial cells include glomerulus endothelial cells, umbilical vein endothelial cells, umbilical artery endothelial cells, coronary artery endothelial cells, saphenous vein endothelial cells, pulmonary artery endothelial cells, aortic endothelial cells, dermal vascular endothelial cells, dermal microvascular endothelial cells, bladder microvascular endothelial cells, uterine microvascular endothelial cells, pulmonary microvascular endothelial cells, cardiac microvascular endothelial cells, dermal microlymphatic endothelial cells, carotid artery endothelial cells, and liver sinusoidal endothelial cells. Vascular endothelial cells may be derived from a human, or an animal other than humans. Examples of the animal other than humans include mice, rats, dogs, monkeys, swine, chimpanzees, goats, and cows. In an embodiment, the animal is preferably a mouse. In an embodiment, vascular endothelial cells are preferably those derived from a human. Vascular endothelial cells isolated from a living body may be used, or commercially available vascular endothelial cells may also be suitably selected for use.

Clonal embryonic kidney cells are not particularly limited, as long as kidney-like microspheres can be formed by co-culturing the clonal embryonic kidney cells together with mesenchymal stem cells and vascular endothelial cells. Examples of clonal embryonic kidney cells include human embryonic kidney cells (HEK293) and mouse embryonic kidney cells (M15).

It is preferred that mesenchymal stem cells, vascular endothelial cells, and clonal embryonic kidney cells are derived from the same animal species. For example, when clonal embryonic kidney cells are derived from a human, mesenchymal stem cells and vascular endothelial cells are preferably derived from a human. Likewise, when clonal embryonic kidney cells are derived from a mouse, mesenchymal stem cells and vascular endothelial cells are preferably derived from a mouse.

In an embodiment, mesenchymal stem cells, vascular endothelial cells, and clonal embryonic kidney cells may be obtained by inducing differentiation of iPS cells or ES cells in vitro. In a preferable embodiment, mesenchymal stem cells, vascular endothelial cells, and clonal embryonic kidney cells are those obtained by not inducing differentiation from iPS cells or ES cells in vitro from the standpoint of work efficiency and risk of developing cancer. For the same reason, the cell group that is subjected to co-culture preferably does not contain iPS cells, ES cells, or cells prepared by inducing differentiation of these cells in vitro.

The cell group that is subjected to co-culture may contain any cells other than mesenchymal stem cells, vascular endothelial cells, and clonal embryonic kidney cells, as long as a kidney-like tissue can be formed. In an embodiment, however, it is preferred that the cell group does not substantially contain cells other than these three types of cells. The phrase "does not substantially contain" means that such cells are allowed to be present in an amount that is inevitably present, even if they are not artificially added. For example, the phrase "does not substantially contain" means that such cells are present in an amount of 1000 or less, 100 or less, 50 or less, 25 or less, 10 or less, or 5 or less, per 2 ml of a culture solution.

The co-culture of the cell group containing mesenchymal stem cells, vascular endothelial cells, and clonal embryonic kidney cells can be performed under any conditions, as long as a kidney-like tissue (microspheres) is prepared. The medium for use is, for example, a medium suitable for culturing mesenchymal stem cells, vascular endothelial cells, and/or clonal embryonic kidney cells. Mediums suitable for culturing these cells are commercially available, and such mediums are suitably selected for use. In an embodiment medium, for example, a 10% FCS-containing medium or a medium prepared by adding an antibiotic and glutamic acid to a medium for mesenchymal stem cell culture (HSCGM) may be used.

The medium for use in co-culture may contain optional components, as long as a kidney-like tissue is obtained. Examples of such components include cytokines, such as BMP4, BMP7, FGF2, FGF9, RA (retinotic acid), activin, and Noggin; and differentiation inducers, such as Wnt inhibitor (e.g., CHIR), BMP inhibitor (e.g., Dorsomorphin), cAMP activator (e.g., Forskolin), and ROCK inhibitor (e.g., Y27632). In an embodiment, the medium preferably does not contain at least one member of these components, or none of them.

The culture temperature is not particularly limited, as long as a kidney-like tissue is obtained. For example, the culture is preferably performed at around 37° C. The culture is preferably performed in 5% $CO_2$.

The amount of the cells of each type subjected to co-culture is not particularly limited, as long as a kidney-like tissue is obtained. For example, the amount of mesenchymal stem cells for use is $1.0 \times 10^2$ to $1.0 \times 10^6$, and preferably $1.0 \times 10^3$ to $1.0 \times 10^5$, per 2 ml of a liquid medium. The amount of vascular endothelial cells for use is, for example, $1.0 \times 10^3$ to $1.0 \times 10^7$, and preferably $1.0 \times 10^4$ to $1.0 \times 10^6$, per 2 ml of a liquid medium. The amount of clonal embryonic kidney cells for use is $1.0 \times 10^2$ to $1.0 \times 10^6$, and preferably $1.0 \times 10^3$ to $1.0 \times 10^5$, per 2 ml of a liquid medium. In an embodiment, the cell count ratio of mesenchymal stem cells to clonal embryonic kidney cells (mesenchymal stem cell: clonal embryonic kidney cells) is preferably 1:10 to 10:1, more preferably 1:5 to 5:1, and still more preferably 1:3 to 3:1.

The culture time period is not particularly limited, as long as a kidney-like tissue is obtained. For example, from the standpoint of production efficiency, the culture time period is preferably 48 hours or less, 42 hours or less, 36 hours or less, 30 hours or less, 24 hours or less, 22 hours or less, 20 hours or less, or 18 hours or less.

The kidney-like tissue obtained under the conditions described above preferably has characteristics equivalent to those of kidneys in vivo. For example, the kidney-like tissue is preferably positive for expression of the following genes: WT1, nephrin, podxl (podocalyxin), podocin, Actn4, CD2AP, Synaptopodin, PTPRO, CDH1, CDH2, and Ngal. A kidney-like tissue that has been formed from mesenchymal stem cells, vascular endothelial cells, and clonal embryonic kidney cells, and that is suitable for use as a model for podocytes is preferably positive for expression of WT1, nephrin, podxl (podocalyxin), podocin, Actn4, CD2AP, Synaptopodin, and PTPRO. A kidney-like tissue that has been formed from mesenchymal stem cells, vascular endothelial cells, clonal embryonic kidney cells, renal tubular cells, and mesangial cells, and that has the characteristics of the renal tubular is preferably positive for expression of all of the 11 types of genes described above. After being formed into microspheres, the kidney-like tissue preferably does not undergo cell proliferation, and preferably maintains homeostasis as a single tissue.

In an embodiment, the cell group containing mesenchymal stem cells, vascular endothelial cells, and clonal embryonic kidney cells preferably further contains renal tubular cells and/or mesangial cells. The type of renal tubular cells is not particularly limited, as long as a renal tubular-like morphology is formed inside the kidney-like tissue. For example, renal tubular cells for use may be renal proximal tubular epithelial cells. The renal tubular cells for use may be derived from a human, or an animal other than humans. Examples of the animal other than humans include mice, rats, dogs, monkeys, swine, chimpanzees, goats, and cows. In an embodiment, the animal is preferably a mouse. In an embodiment, renal tubular cells are preferably those derived from a human. Renal tubular cells isolated from a living body may be used, or commercially available renal tubular cells may also be suitably selected for use.

The type of mesangial cells may be any type, and is not particularly limited, as long as a kidney-like tissue is formed by co-culturing the mesangial cells together with mesenchymal stem cells, vascular endothelial cells, and clonal embryonic kidney cells. Mesangial cells may be those derived from a human, or an animal other than humans. Examples of the animal other than humans include mice, rats, dogs, monkeys, swine, chimpanzees, goats, and cows. In an embodiment, the animal is preferably a mouse. In an embodiment, mesangial cells are preferably those derived from a human. Mesangial cells isolated from a living body may be used, or commercially available mesangial cells may also be suitably selected for use.

The amount of renal tubular cells and mesangial cells subjected to co-culture is not particularly limited, as long as a kidney-like tissue that has desired renal tubular characteristics is obtained. For example, the amount of renal tubular cells for use is $1.0 \times 10^2$ to $1.0 \times 10^6$, and preferably $1.0 \times 10^3$ to $1.0 \times 10^5$, per 2 ml of a liquid medium; and the amount of mesangial cells for use is $1.0 \times 10^2$ to $1.0 \times 10^6$, and preferably $1.0 \times 10^3$ to $1.0 \times 10^5$, per 2 ml of a liquid medium.

The mesenchymal stem cells, vascular endothelial cells, clonal embryonic kidney cells, renal tubular cells, and mesangial cells for use in forming a kidney-like tissue may have any exogenous gene introduced therein. In an embodiment, a kidney-like tissue is preferably formed by using clonal embryonic kidney cells into which an exogenous gene is introduced. Such a kidney-like tissue can be used in, for example, screening for a substance that affects the function of podocytes. In another embodiment, a kidney-like tissue is preferably formed by using renal tubular cells into which an exogenous gene is introduced. Such a kidney-like tissue can be used in, for example, screening for a substance that causes renal tubular disorder and/or a substance useful in the treatment of renal tubular disorder.

The type of the exogenous gene can be suitably selected depending on the purpose, and is not particularly limited. In an embodiment, the exogenous gene is preferably a marker gene. The "marker gene" as used here refers to a gene usable as an indicator for detection of the expression of a specific gene. Examples of such a marker gene include fluorescent protein genes, luciferase genes, β-glucuronidase genes, β-galactosidase genes, thymidine kinase genes, diphtheria toxin genes, and drug-resistant genes.

For example, by using a kidney-like tissue formed with embryonic kidney cells into which a marker gene (e.g., a fluorescent protein) is introduced downstream of a gene that plays a key role in the function of the kidney tissue, such as WT1, screening for a substance that affects the expression of WT1 gene can be efficiently performed with the marker gene as an indicator. Specifically, screening can be performed by adding a candidate substance to a kidney-like tissue, and comparing the gene expression profile of the kidney-like tissue before the addition of the candidate substance with the gene expression profile of the kidney-like tissue after the addition of the candidate substance. The introduction of a marker gene in this manner can be performed using a genome editing technique by inserting a marker gene into the locus and the expression regulation domain, such as the promoter and the enhancer, of a target gene; and then screening for a substance can be performed. As described here, the kidney-like tissue is usable as a kidney model.

The kidney-like tissue (microspheres) is also usable in screening for a therapeutic agent for renal dysfunction. For example, a therapeutic agent (or promising substance) can be screened by allowing the kidney-like tissue to be present in the presence of a candidate substance, measuring gene expression levels associated with kidney function, and comparing the measured expression levels (profile) with gene expression levels in the absence of the candidate substance. The type of gene associated with kidney function usable in screening is not limited. In an embodiment, the gene associated with kidney function is preferably at least one member selected from the group consisting of nephrin (NPHS1), podocin (NPHS2), PLCE1, Arhgap24, Myo1E, MYH9, INF2, ARHGDIA, ANLN, wt1 (wilms tumor-1), LMX1B, SMARCAL1, synaptopodin, CD2AP, GLEPP-1NEPH1, NEPH2, podocalyxin, α-Actinin-4, α-dystroglycan, Nestin, Vimentin, MAGI2, IQGAP2, TRPC6, CASK, CD31, podoplanin, Ezrin, ZO-1, FAT, and P-cadherin. The kidney-like tissue may be a healthy kidney model, or a kidney model with renal dysfunction. In an embodiment, the kidney-like tissue is preferably a kidney model with renal dysfunction. A kidney model with renal dysfunction can be prepared by any technique. For example, a diabetes model can be prepared by exposing a kidney-like tissue to high-blood sugar conditions. A nephritis model can be prepared by exposing a kidney-like tissue to inflammatory cytokines. A drug-induced acute renal damage model can be prepared by exposing a kidney-like tissue to a medicinal agent, such as cisplatin.

EXAMPLES

The present invention is described below in more detail with reference to Examples. However, the present invention is not limited thereto.

1. Production of Kidney Organoids (Microspheres) Using Three Kinds of Cells

Endothelial cells (HUVEC) and human mesenchymal stem cells (hMSC) were co-cultured with human embryonic kidney cells (HEK) to produce kidney-like organoids in vitro. $5 \times 10^4$ hMSCs, $2 \times 10^5$ HUVECs, and $5 \times 10^4$ HEKs were suspended in 2 ml of 10% FCS or MSCGM and seeded in a MicroWell culture plate. After incubation in a 5% $CO_2$ humidified incubator at 37° C. for 24 hours, formation of cell aggregates (kidney-like microspheres) was observed (FIG. 1). In contrast, monoculture of HEK produced aggregates with a slightly twisted shape. The resulting kidney-like microspheres maintained their spherical morphology for 20 days or longer.

2. Analysis of Gene Expression

Figure 2:
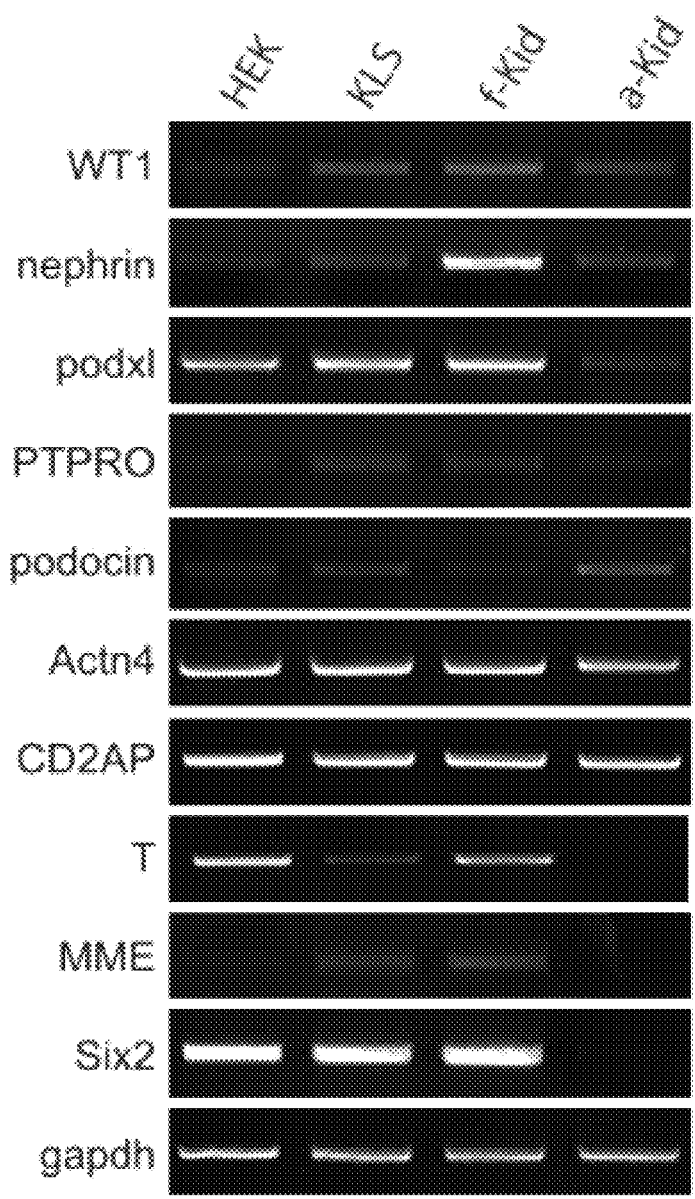
FIG. 2 shows gene expression profiles of aggregate tissue obtained by monoculture of human embryonic kidney cells; and kidney-like tissue obtained by co-culture of endothelial cells, mesenchymal stem cells, and human embryonic kidney cells.

RT-PCR analysis was performed on mRNAs of kidney-like microspheres and aggregates obtained by monoculture of HEK. Total RNA was extracted from the spheres using a TRIzol reagent (Invitrogen), and reverse-transcribed with an oligo (dT) primer using a SuperScript First-Strand Synthesis kit (Invitrogen) to produce first-strand cDNA. Subsequently, PCR was performed to detect the expression of podocyte-specific gene and GAPDH. Gene expression in human embryonic kidney (Agilent Technologies, Inc.) and human adult kidney (Agilent Technologies, Inc.) as comparative subjects was also examined in the same manner. The results confirmed that transcription markers typical of podocytes (e.g., WT 1) and important structural markers, such as podocin and nephrin, are constitutively expressed in kidney-like microspheres (FIG. 2). The gene expression profile of kidney-like microspheres was considered to be an intermediate between the gene expression profile in human embryonic kidney, and the gene expression profile in human adult kidney. Table 1 below shows sequences of the primers used in the RT-PCR analysis.

TABLE 1

| Marker | Primer F | | Primer R | |
|---|---|---|---|---|
| Nephrin | GGACATAGTCTGCACTGTCGAT | SEQ ID NO: 1 | GGCAAATCTGACAACAAGACG | SEQ ID NO: 2 |
| WT1 | GTACGAGAGCGATAACCACACA | SEQ ID NO: 3 | GGCTTTTCACCTGTATGAGTCC | SEQ ID NO: 4 |
| CD2AP | AAAACCAAAGAAACCACCACCT | SEQ ID NO: 5 | GGCATCTTTGGTCTATTTGCAG | SEQ ID NO: 6 |

TABLE 1-continued

| Marker | Primer F | | Primer R | |
|---|---|---|---|---|
| Podxl | CTATCCCTGGCTACACCTTCAC | SEQ ID NO: 7 | CTCGGCATATCAGTGAGATCAA | SEQ ID NO: 8 |
| Podocin | GCTACTACCGAATGGAAAATGC | SEQ ID NO: 9 | AGTTCTGTTGCTGGGAGAAGAC | SEQ ID NO: 10 |
| Six2 | GAGCACCTTCACAAGAATGAAA | SEQ ID NO: 11 | ATTGGAGTTCTCGTTGTTCTCC | SEQ ID NO: 12 |
| Actn4 | TGCACAAAATCAACAATGTGAA | SEQ ID NO: 13 | TTCTCGTAGTCCTCCATCAGGT | SEQ ID NO: 14 |
| MME | GTCCTTCAAGAACCCAAAACTG | SEQ ID NO: 15 | CAATCTGGCCACAGAAATCATA | SEQ ID NO: 16 |
| PTPRO | TAACCCTGCTACCCTCATGTCT | SEQ ID NO: 17 | TCCACAGTGATGTCTCCATAGG | SEQ ID NO: 18 |
| T | AGGAGCTCACCAATGAGATGAT | SEQ ID NO: 19 | TCCTCGTTCTGATAAGCAGTCA | SEQ ID NO: 20 |
| GAPDH | CCACCCATGGCAAATTCCATGGCA | SEQ ID NO: 21 | TCTAGACGGCAGGTCAGGTCCACC | SEQ ID NO: 22 |

3. Analysis by Cell Staining

Figure 3:
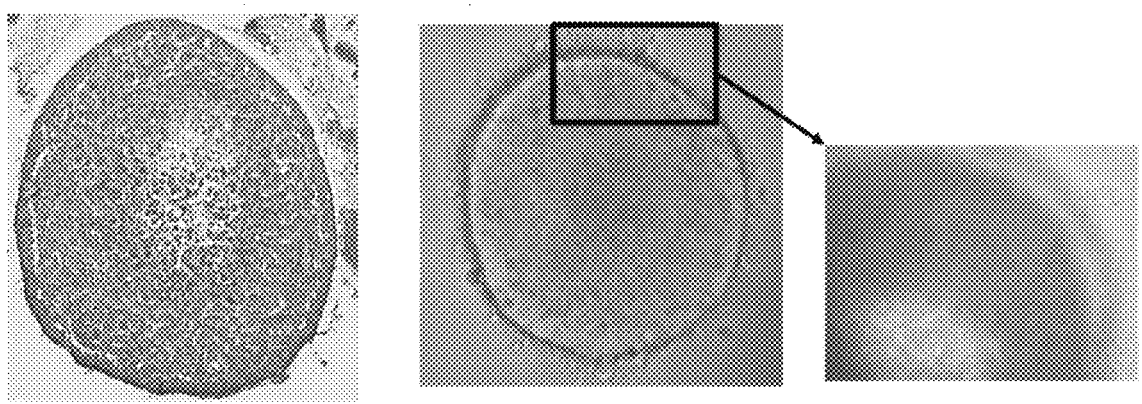
FIG. 3 shows confocal laser scanning microscopy images of kidney-like tissue (kidney-like microspheres) obtained by co-culture of endothelial cells, mesenchymal stem cells, and human embryonic kidney cells.

Immunohistochemical staining using antibodies against cell-type-specific marker proteins was performed to determine the localization of three different cell types at early and late stages of kidney-like microsphere formation. Kidney-like microspheres were centrifuged at 1000 rpm for 5 minutes. The kidney-like microspheres were collected using iPGell (Geno Staff Co., Ltd.), fixed with 4% paraformaldehyde (PFA) for 1 hour; and immersed in 10% sucrose for 4 hours, in 20% sucrose for 4 hours, and then in 30% sucrose overnight, following the manufacturer's instructions. Subsequently, the spheres were embedded in an Optimal Cutting Temperature compound (Sakura FineTek Japan Co., Ltd.), and sectioned to a thickness of 10 μm on a cryostat (Leica CM 3050 S; Leica Microsystems, IL, USA). These sections were subjected to HE staining, and images were obtained with a confocal laser scanning microscope (LSM 780; Carl Zeiss, Jena, Germany). Further, the spheres themselves were imaged with a phase-contrast microscope (FIG. 3). The results showed that different cell types are not merely randomly distributed in organoids, but that the cells begin to rapidly form a structure having reproducible spatial distribution of podocytes and endothelial cells. In contrast, MSC (stained with vimentin) was randomly distributed between podocytes and endothelial cells. Taken together, the podocytes induced in vitro not only have traits as non-proliferating cells in normal adult bodies, but also have typical characteristics of in vivo podocytes in the transcription profile.

4. Confirmation of Blood Vessel Formation

Figure 4:
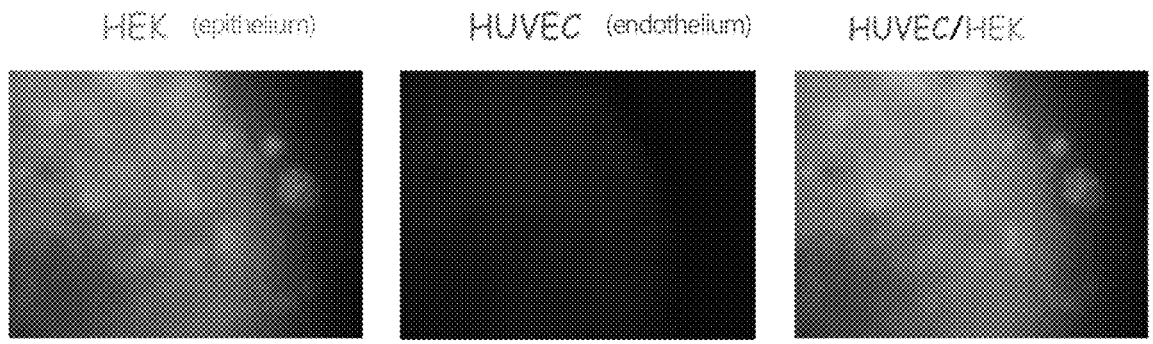
FIG. 4 shows the results of confirming blood vessel formation in kidney-like microspheres.

The present inventors tested whether glomeruli produced from kidney-like microspheres integrate with vascular endothelial cells. To visualize the formation of endothelial sprouts in kidney-like microspheres, DAPI labeling (Wako Pure Chemical Industries, Ltd.) was introduced into HUVEC. Blood vessel formation by HUVEC in the produced three-dimensional tissue was confirmed (FIG. 4).

5. Renal Function Evaluation

Figure 5:
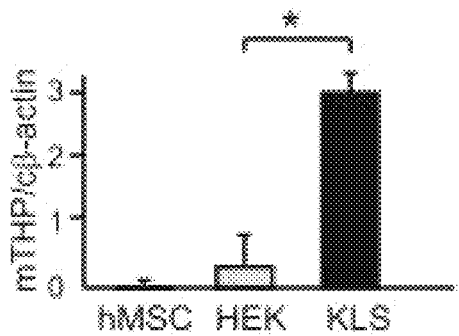
FIG. 5 shows the results of measuring the amount of uromodulin (THP) secretion per kidney-like microsphere.

To evaluate the maintenance of human renal function, human uromodulin production was assessed by Western blotting. After proteins were extracted from the kidney-like microspheres, the culture solution was collected, and the amount of uromodulin (THP) secretion per microsphere was compared. β-actin was used as a control. The amount of uromodulin in the co-culture medium was higher than that obtained by monoculture of HEK on day 7. The results affirmed stromal cell dependent assistance in maintaining renal function (FIG. 5).

6. Preparation of Kidney Microspheres Using Five Kinds of Cells

Figure 6:
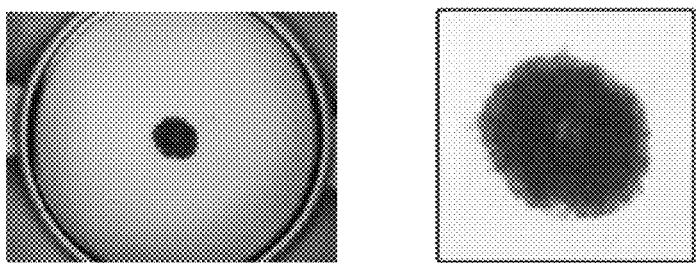
FIG. 6 shows that kidney-like microspheres were formed by co-culture of endothelial cells, mesenchymal stem cells, human embryonic kidney cells, human mesangial cells, and human renal tubular cells.

Kidney-like organoids were produced in vitro by co-culturing endothelial cells (HUVEC), mesenchymal stem cells (hMSC), and human embryonic kidney cells (HEK) with human mesangial cells (hMC) and human renal tubular cells (HK2). $5 \times 10^4$ hMSC, $2 \times 10^5$ HUVEC, $5 \times 10^4$ HEK, $5 \times 10^4$ hMC, and $5 \times 10^4$ HK 2 were suspended in 2 ml 10% FCS or MSCGM, and seeded in a MicroWell culture plate. After incubation in a 5% $CO_2$ humidified incubator at 37° C. for 24 hours, formation of cell aggregates and microspheres was observed (FIG. 6). The resulting kidney-like microspheres maintained their spherical morphology for 20 days or longer.

7. Analysis of Gene Expression

RT-PCR analysis was performed on mRNA of kidney-like microspheres using five types of cells. Total RNA was extracted from the spheres using a TRIzol reagent (Invitrogen), and reverse-transcribed with an oligo (dT) primer using a SuperScript First-Strand Synthesis kit (Invitrogen) to produce first-strand cDNA. Subsequently, PCR was performed to detect the expression of renal tubular cell-specific genes, renal tubular injury marker (epithelial-mesenchymal transition (EMT)) genes, and GAPDH. The results confirmed that renal tubular cell-specific genes (CDH1, CDH2, Ngal, and CLU) were constitutively expressed; that their expression was reduced by cisplatin, a representative pharmaceutical agent for renal tubular injury; and that changes in EMT were reproduced in the spheres (the left side of FIG. 7). The influence of cisplatin was analyzed by adding cisplatin to the culture solution to a final concentration of 5 μM, and extracting RNA after 3 hours and after 24 hours for analysis. Tables 1 and 2 below show sequences of the primers used in the RT-PCR analysis.

TABLE 2

| Marker | Primer F | | Primer R | |
|---|---|---|---|---|
| Kim1 | AGAAGGGATGTCTCTTTGACCA | SEQ ID NO: 23 | CTGGTGGGTTCTCTCCTTATTG | SEQ ID NO: 24 |
| Ngal | GAACTTCCAGGACAACCAATTC | SEQ ID NO: 25 | CCTTTAGTTCCGAAGTCAGCTC | SEQ ID NO: 26 |

TABLE 2-continued

| Marker | Primer F | | Primer R | |
|---|---|---|---|---|
| CLU | GCCCTTCCTTGAGATGATACAC | SEQ ID NO: 27 | CAGTGATGGGATCAGAGTCAAA | SEQ ID NO: 28 |
| CDH1 | TTAGAGGTCAGCGTGTGTGACT | SEQ ID NO: 29 | GGAGTTCAGGGAGCTCAGACTA | SEQ ID NO: 30 |
| CDH2 | CAAACCAATCGACTTTGAAACA | SEQ ID NO: 31 | GGAAGATCAAAAGCAAATGGTC | SEQ ID NO: 32 |
| Jag1 | AATGAATGCCAGTCTTCACCTT | SEQ ID NO: 33 | AGACCTGGTGACATCATCTCCT | SEQ ID NO: 34 |

Figure 7:
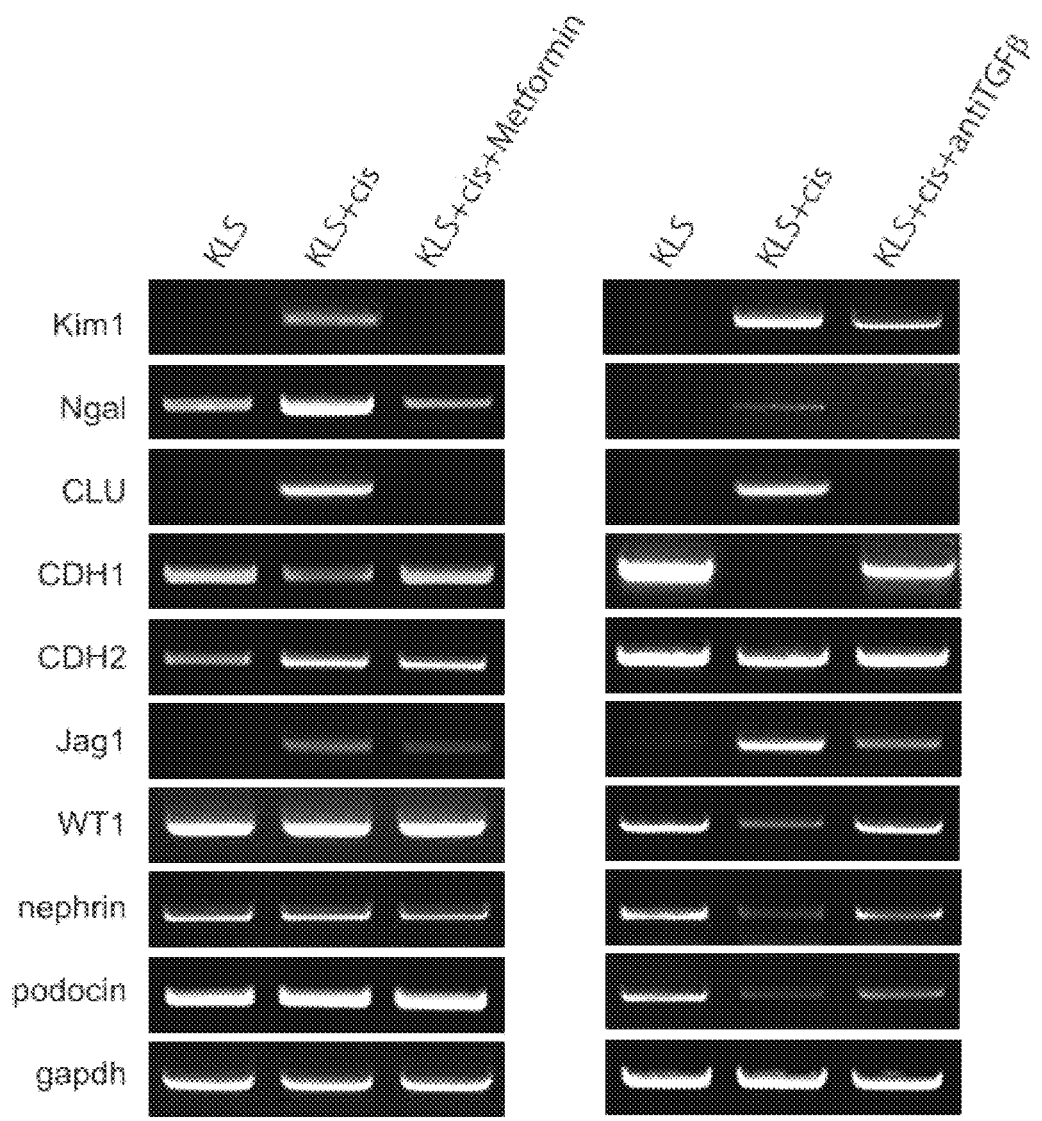
FIG. 7 shows gene expression profiles of kidney-like microspheres (KLS) obtained by co-culture of endothelial cells, mesenchymal stem cells, human embryonic kidney cells, human mesangial cells, and human renal tubular cells; and the influence of cisplatin (cis), metformin, or TGFl13 neutralizing antibody on the gene expression in kidney-like microspheres (KLS).

Renal tubular injury caused by cisplatin is presented as acute kidney injury. If the renal tubular injury becomes chronic, not only are renal tubular cells damaged, but podocyte injury also occurs. This becomes the main cause of irreversible renal hypofunction. Analysis of long-term administration of cisplatin confirmed a reduction in the expression of genes constitutively expressed in podocytes (FIG. 7). The results showed that an injury model aggravated from acute kidney injury to renal failure, for which there is no solution at present, can be constructed by using these spheres.

8. Use of Microspheres as Kidney Model (Acute kidney Injury)

For acute renal tubular injury as acute kidney injury caused by cisplatin (3 hours after administration), pre-administration of metformin, which functions as a competitor of a cisplatin transporter OCT2 in renal tubular cells, inhibited abnormal changes in gene expression in acute kidney injury (the left side of FIG. 7). It is known that podocyte injury occurs during the progression from acute kidney injury to irreversible renal hypofunction. In these spheres as well, reduced expression of genes indispensable for homeostasis of podocytes was confirmed. Such podocyte injury as chronic kidney disease caused by cisplatin (24 hours after administration) was confirmed to be inhibited by pre-administration of the neutralizing antibody against TGFβ1, which is a cause of podocyte injury (the right side of FIG. 7).

9. Production of Kidney-like Organoids (Microspheres) Using Mouse Cells

Figure 8:
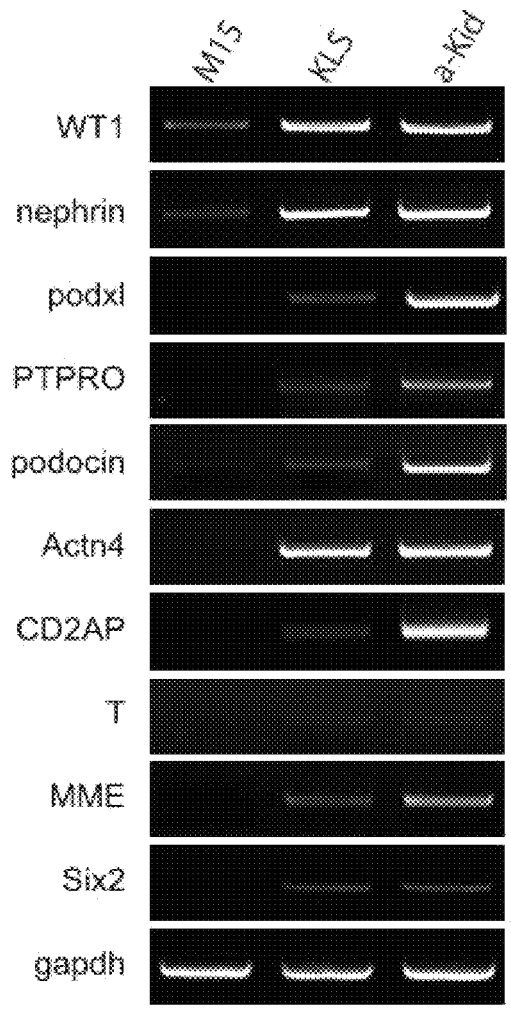
FIG. 8 shows gene expression profiles in aggregate tissues obtained by monoculture of mouse embryonic kidney cells; or co-culture of mouse-derived endothelial cells, mesenchymal stem cells, and embryonic kidney cells.

Kidney-like organoids were produced in vitro using mouse cells. As a result, formation of products similar to human cellular aggregates and microspheres was observed (FIG. 8). The resulting kidney-like microspheres maintained their spherical morphology for 10 days or longer. Kidney-like organoids were produced by co-culturing endothelial cells (MSS31), mesenchymal stem cells (C3H10T1/2), and mouse embryonic kidney cells (M15). $5 \times 10^4$ C3H10T1/2, $2 \times 10^5$ MSS31, and $5 \times 10^4$ M15 were suspended in 2 ml of 10% FCS or MSCGM, and seeded in a MicroWell culture plate. After incubation in a 5% $CO^2$ humidified incubator at 37° C. for 24 hours, formation of kidney-like organoids was observed. RT-PCR analysis was performed on mRNAs of kidney-like microspheres and aggregates obtained by mon-oculture of M15, and mRNA extracted from 5-week-old mouse kidney. Total RNA was extracted from kidney-like microspheres using a TRIzol reagent (Invitrogen), and reverse-transcribed with an oligo (dT) primer using a Super-Script First-Strand Synthesis kit (Invitrogen) to produce first-strand cDNA. Subsequently, PCR was performed to detect the expression of podocyte-specific gene and GAPDH. The results confirmed that transcription markers typical of podocytes (e.g., WT1) and important structural markers, such as podocin and nephrin, were constitutively expressed (FIG. 8). Table 3 below shows sequences of the primers used in the RT-PCR analysis.

TABLE 3

| Marker | Primer F | | Primer R | |
|---|---|---|---|---|
| WT1 | CCAGCTTGAATGCATGAC | SEQ ID NO: 35 | CCCAAACTTTTTCTGACAAC | SEQ ID NO: 36 |
| Nephrin | GCTTCTGGGCTCTATCTGAAAA | SEQ ID NO: 37 | GACTAGCAGCTGCCCATTATCT | SEQ ID NO: 38 |
| Podxl | CTTCTTTCTACCCCCACAACAG | SEQ ID NO: 39 | GGAGAAAGCTTCGTCTCGATAA | SEQ ID NO: 40 |
| PTPRO | ATTTAACAGCACATTGCCTCCT | SEQ ID NO: 41 | ACAGAGATGTTTCGAGGTGGAT | SEQ ID NO: 42 |
| Podocin | CGTCTCCAGACCTTGGAAATAC | SEQ ID NO: 43 | GAGGAACTTGGGTAGTTGATGC | SEQ ID NO: 44 |
| Actn4 | GAAGCCTTGGAGAAAACAGAGA | SEQ ID NO: 45 | CCATTGTGTAGTTGGTGTGCTT | SEQ ID NO: 46 |
| CD2AP | GGAAGAAGGATGGCTAGAAGGA | SEQ ID NO: 47 | TTCACCATCCTCTGTGGACTCT | SEQ ID NO: 48 |
| T | GGTGCTGAAGGTAAATGTGTCA | SEQ ID NO: 49 | AGGCTTTAGCAAATGGGTTGTA | SEQ ID NO: 50 |
| MME | TGATCGCTCTCTATGCAACCTA | SEQ ID NO: 51 | CCAAGAAGTGCAATATGTTTGA | SEQ ID NO: 52 |
| Six2 | GAGACCAGCTACTGCTTCAAGG | SEQ ID NO: 53 | GACATGGGGTTGAGTATGGAGT | SEQ ID NO: 54 |
| GAPHD | TATGACTCCACTCACGGCAAAT | SEQ ID NO: 55 | TGCTTCACCACCTTCTTGATGT | SEQ ID NO: 56 |

10. Use of Microspheres as Kidney Model (Renal Tubular Injury)

Figure 9A:
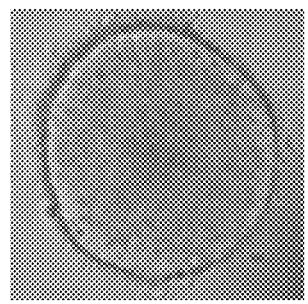
FIG. 9 shows three-dimensional kidney-like tissue formed by co-culturing embryonic kidney cells, mesenchymal stem cells, proximal renal tubular cells, and vascular endothelial cells (FIG. 9(A)); results of measuring β2 microglobulin after exposing the kidney-like tissue to cisplatin at a concentration of 5 μM (FIG. 9(B)); and images capturing changes in shape of the sphere (FIG. 9(C)).
Figure 9B:
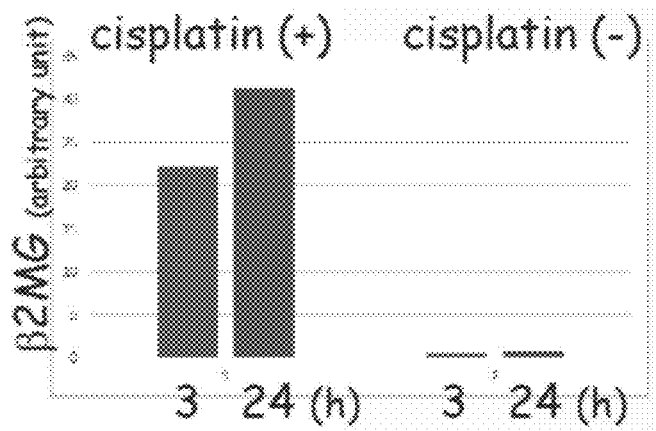
Figure 9C:
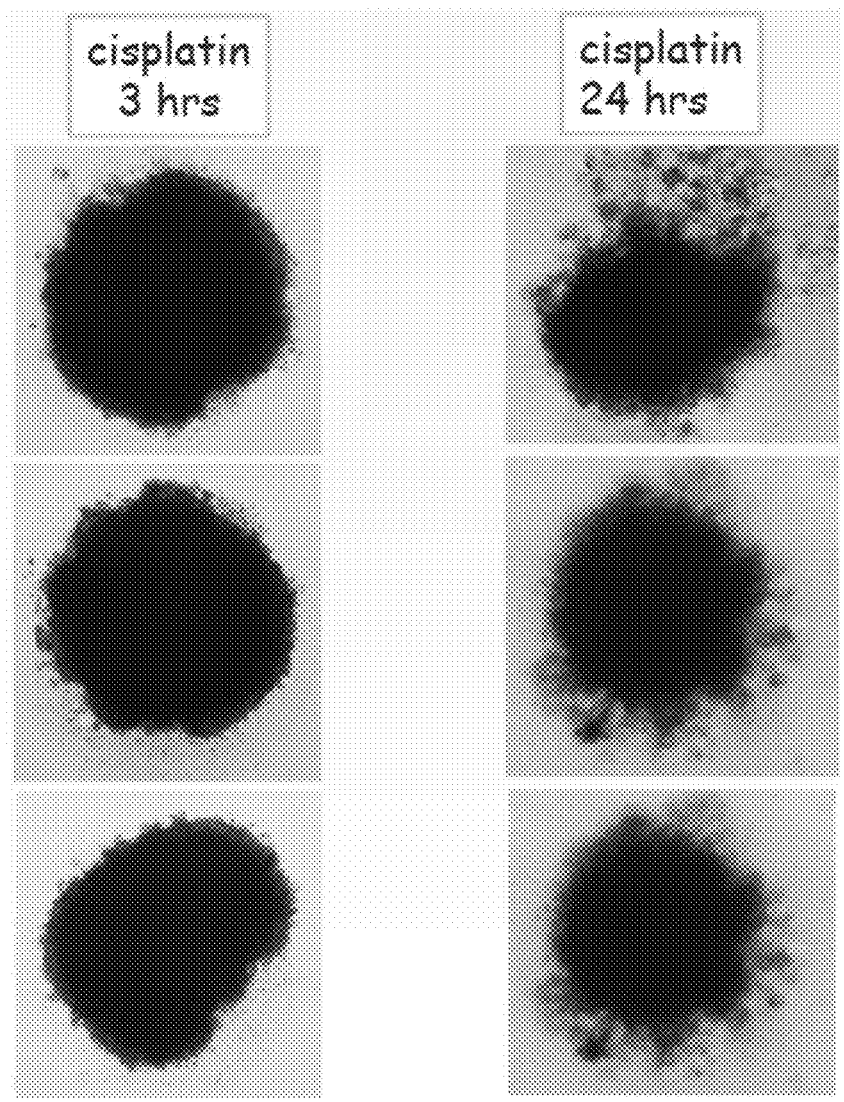

Embryonic kidney cells, mesenchymal stem cells, proximal renal tubular cells, and vascular endothelial cells were co-cultured for 24 hours to obtain a self-organized, three-dimensional kidney-like tissue (FIG. 9 (A)). This was exposed to cisplatin at a concentration of 5 µM, and spheres were collected after 3 hours and after 24 hours. After extraction of RNA, changes in gene expression were analyzed by the RT-PCR method. After the culture solution of the spheres was collected and cell components were separated by centrifugation, β2 microglobulin was measured with a "Lumipulse Presto β2-M" (produced by Fujirebio, Inc.) kit (FIG. 9 (B)). Further, changes in the shape of the spheres were imaged using an optical microscope (FIG. 9 (C)).

This method successfully reproduced extensive renal damage due to chronic phase drugs, which conventional analysis by drug administration to the culture of human proximal renal tubular cells failed to clarify. It was confirmed that the analysis results reflect renal tubular injury at the acute phase and podocyte injury at the chronic phase, and that simultaneous analysis of progressive drug failure in humans can be performed by using the same model.

11. Use of Microspheres as Kidney Model (Podocyte Injury)

Figure 10:
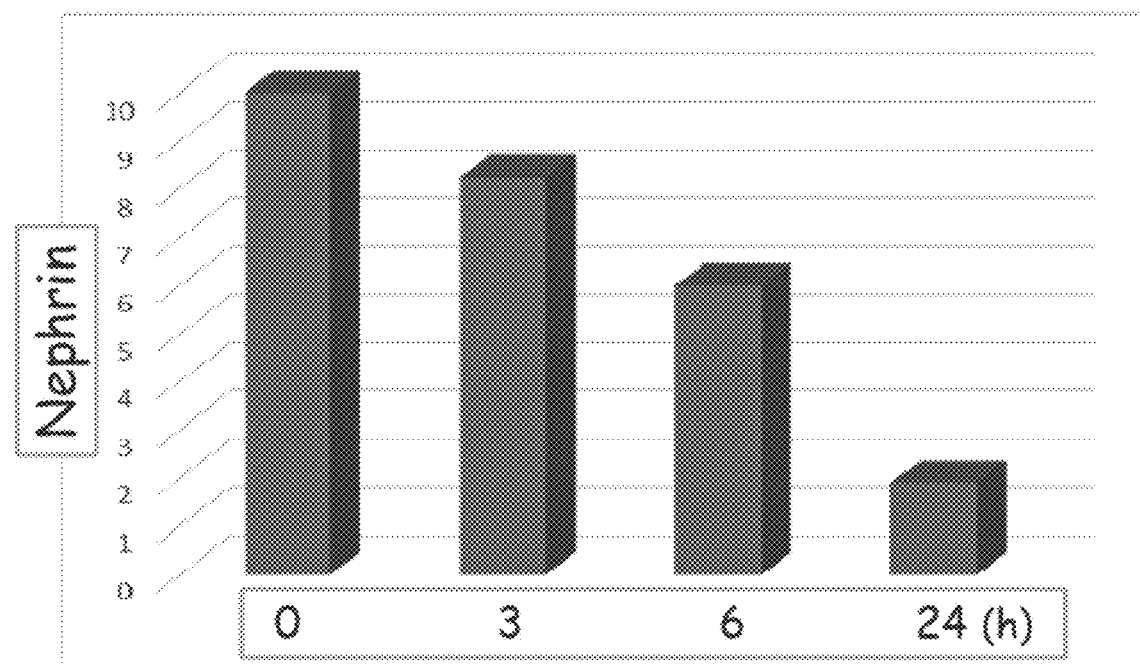
FIG. 10 shows changes in nephrin gene expression by exposing the three-dimensional kidney-like tissue to puromycin.

Embryonic kidney cells, mesenchymal stem cells, and vascular endothelial cells were co-cultured for 24 hours to obtain a self-organized, three-dimensional kidney-like tissue. The kidney-like tissue was exposed to puromycin at a concentration of 50 µg/ml. After 24 hours, spheres were collected. After extraction of RNA, changes in nephrin gene expression were analyzed by the qRT-PCR method (FIG. 10). The analysis results confirmed that a podocyte injury model, which was conventionally prepared by using mice, can be reproduced by using three-dimensional kidney-like tissue. Using this model allows for screening an effective drug for podocyte injury.

Figure 11:
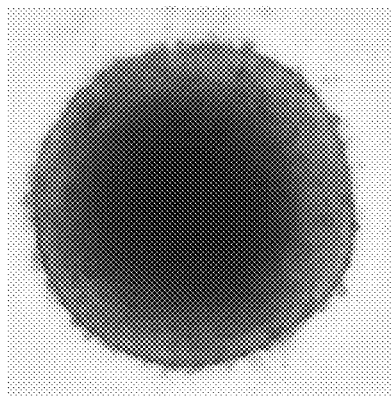
FIG. 11 shows changes in shape (B) after adding the serum of a patient with focal glomerulosclerosis to the three-dimensional kidney-like tissue (A).
Figure 11:
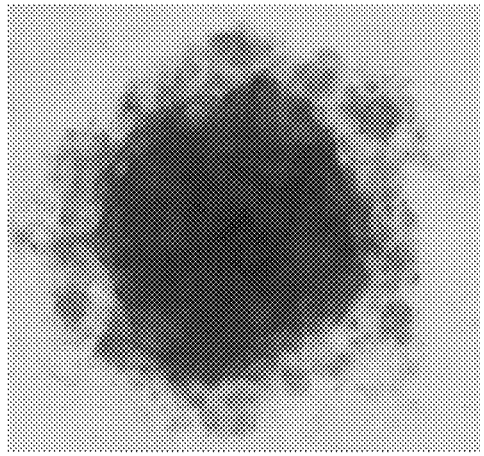
Figure 12A:
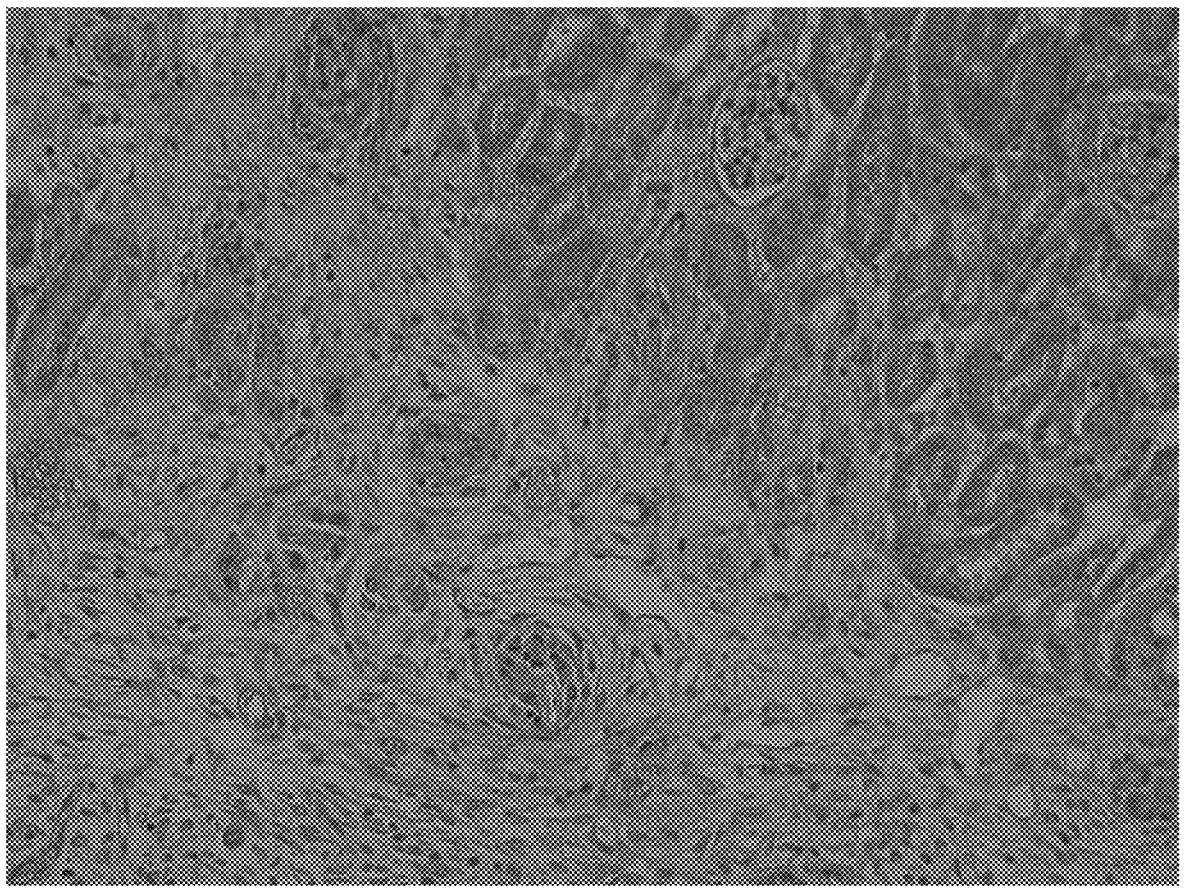
FIG. 12A and FIG. 12B show the presence of erythrocytes in the lumen.
Figure 12B:
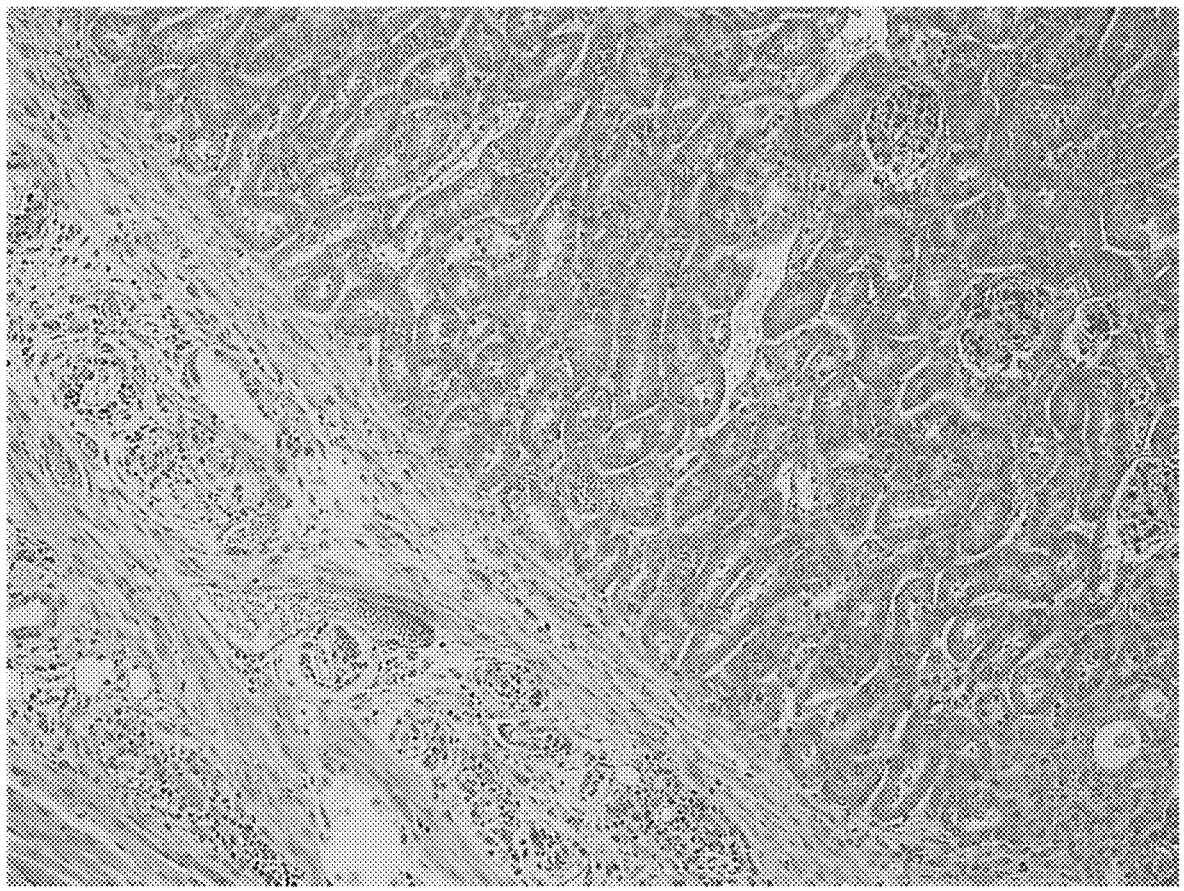
Figure 12C:
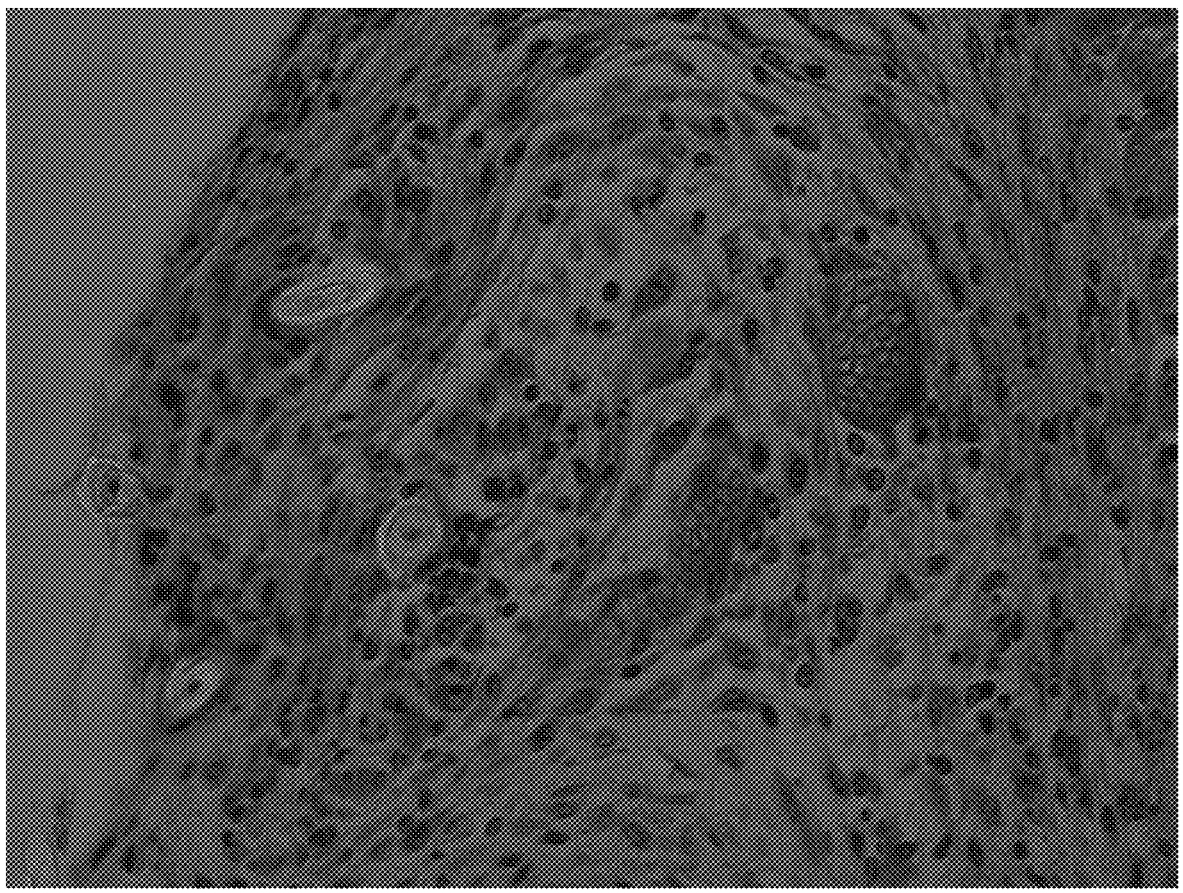
FIG. 12C and FIG. 12D show the presence of lumens, and E and F show the presence of a basement membrane.
Figure 12D:
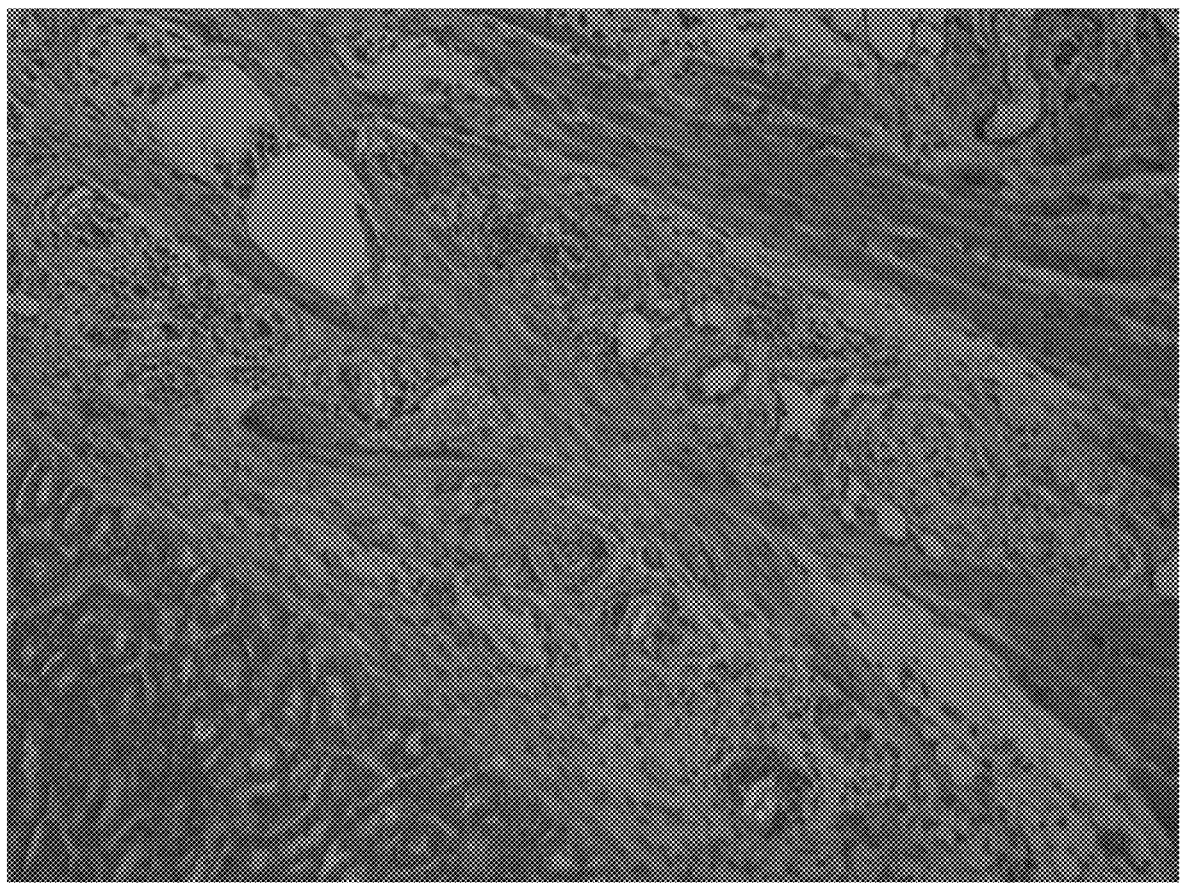
Figure 12E:
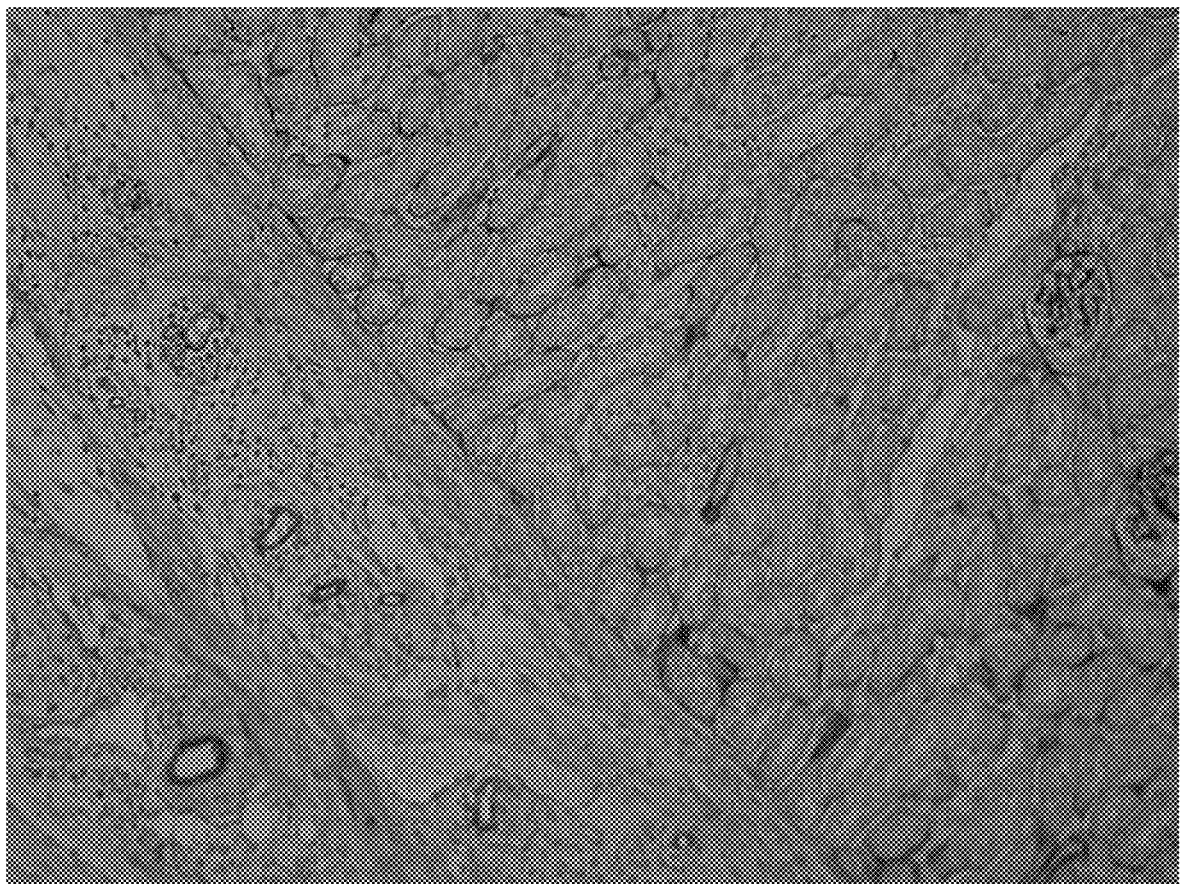
FIG. 12 shows changes in shape and structure after the three-dimensional kidney-like tissue was transplanted to a renal subcapsular space in immunodeficient mice.
Figure 12F:
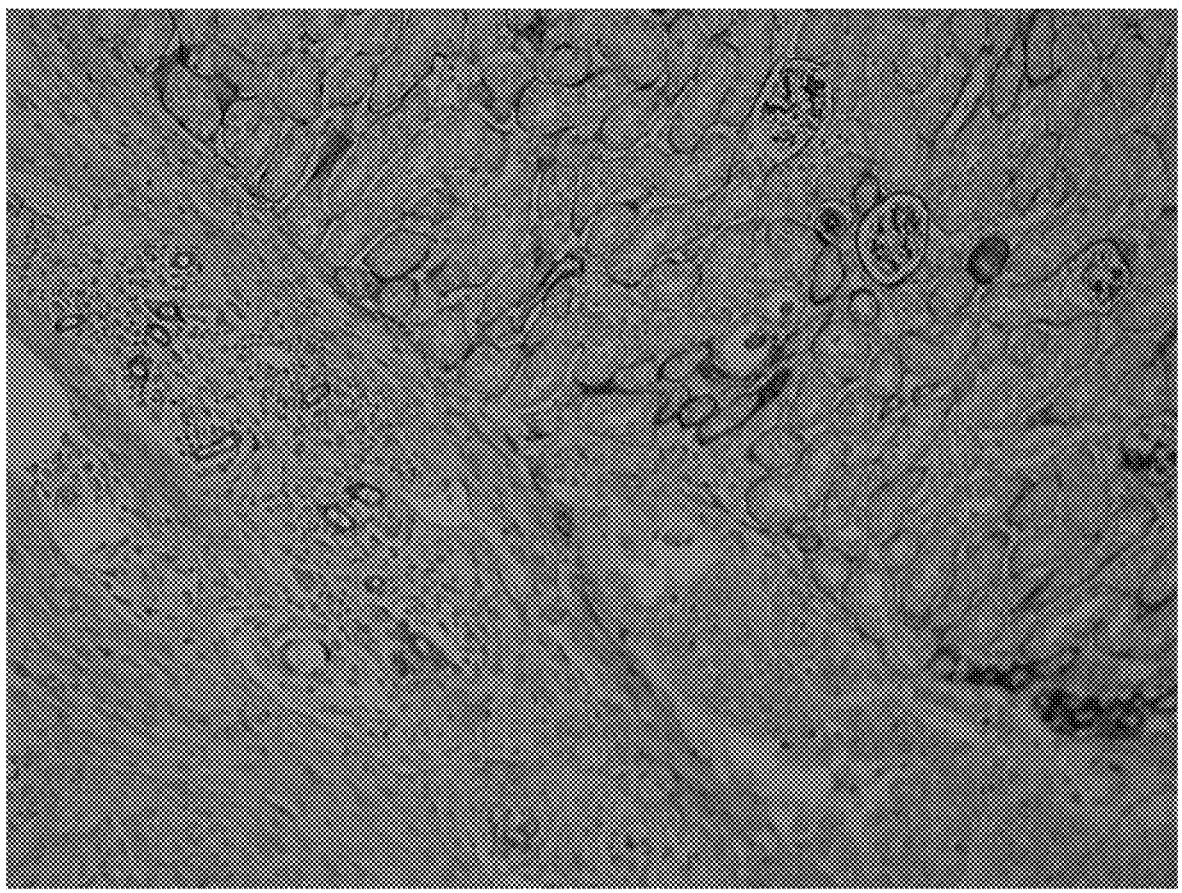

12. Use as Pathophysiological Analysis System for Human Refractory Renal Disease Embryonic kidney cells, mesenchymal stem cells, and vascular endothelial cells were co-cultured for 24 hours to obtain a self-organized, three-dimensional kidney-like tissue (FIG. 11 (A)). The kidney-like tissue was cultured with 5% FCS, and serum of a patient with focal glomerulosclerosis was added to a final concentration of 5% (10% in total). After 10 to 24 hours, changes in the shape of the spheres were imaged using an optical microscope (FIG. 11 (B)). It was confirmed that the form of the microspheres greatly changes due to the influence of components contained in the patient's serum. Therefore, target genes of a refractory renal disease can be identified by collecting spheres, extracting RNA, and comprehensively comparing gene expression with that of the control. Further, using a three-dimensional kidney-like tissue having a normal podocyte gene profile makes it possible to not only clarify podocyte-related genes involved in the cause of refractory kidney disease, but also monitor the genes before and after treatment and during the course of treatment. Thus, the microspheres of the present invention can also be used to determine the effectiveness of therapeutic treatment.

13. Renal Subcapsular Transplantation Method

Embryonic kidney cells, mesenchymal stem cells, and vascular endothelial cells were co-cultured. The potential glomerular structure-forming ability of a self-organized, three-dimensional kidney-like tissue was evaluated by the renal subcapsular transplantation method using immunodeficient mice. Immunodeficient mice (NOD/SCID mice) were used as recipients. After shaving, co-culture was started 24 hours before transplantation to prepare fresh three-dimensional kidney-like tissue. In this process, vascular endothelial cells among the cells used for the co-culture were treated, so that BFP (blue fluorescent protein) could be expressed in the vascular endothelial cells and the vascular endothelial cells could exhibit blue fluorescent color.

After each recipient was anesthetized with inhalational anesthesia and disinfected, the operative field was determined. First, two agarose rods were inserted so as not to collapse the spherical shape of a graft, and a space for receiving a graft was created under the kidney capsule. The three-dimensional kidney-like tissue to be transplanted was inserted until it was completely covered by the capsule. The kidney was returned to the abdominal cavity, and the incision site was closed. The resulting immunodeficient mice were then raised in a usual manner. Ten days after the transplantation, the kidney containing the graft was removed. After paraffin embedding, various types of staining were performed. HE staining observation showed the presence of a glomerular-like structure in the graft and confirmed that the glomerular-like structure had a lumen structure therein, and that erythrocytes were present in the lumen (FIG. 12 (A, B)). Further, fluorescence observation showed blue fluorescence located in accordance with lumens (FIG. 12 (C, D)). Further, PAM staining observation showed the presence of a basement membrane (FIG. 12 (E, F)).

The results reveal that differentiation of the three-dimensional kidney-like tissue formed using embryonic kidney cells, mesenchymal stem cells, and vascular endothelial cells was further promoted under the kidney capsule, and a well-defined vasculature was induced; and that this vasculature was formed of the introduced vascular endothelial cells, rather than recipient-derived cells. Further, since formation of a vascular basement membrane and inflow of erythrocytes were also confirmed, the results suggest that a glomerular structure capable of filtering the recipient's blood can be formed if more time passes. This method is not invasive, unlike organ transplantation, and can be performed repeatedly. Further, this method can be a therapeutic tool with a considerably low risk of developing cancer, unlike transplantation using pluripotent stem cells.

The invention claimed is:

1. A method for producing a kidney-like tissue, the method comprising:
co-culturing a cell group containing a mesenchymal stem cell, a vascular endothelial cell, and a clonal embryonic kidney cell to generate tissues, and
selecting from the tissues, as a kidney-like tissue, a microsphere positive for expression of at least one member selected from the group consisting of Wilms tumor-1, nephrin, and podocin.

2. The method according to claim 1, wherein the mesenchymal stem cell, the vascular endothelial cell, and the clonal embryonic kidney cell are derived from a human or a mouse.

3. The method according to claim 1, wherein the clonal embryonic kidney cell is HEK cell or M15 cell.

4. The method according to claim 1, wherein the cell group is free from iPS cell, ES cell, and/or a differentiation-induced cell thereof.

5. The method according to claim 1, wherein the co-culture is performed for 12 hours or more, and 36 hours or less.

6. The method according to claim 1, wherein the cell count ratio of the mesenchymal stem cell to the clonal embryonic kidney cell (mesenchymal stem cell:clonal embryonic kidney cell) is 1:10 to 10:1.

7. A method for producing a kidney-like tissue, the method comprising:
co-culturing a cell group containing a mesenchymal stem cell, a vascular endothelial cell, and a clonal embryonic kidney cell,
wherein the cell group further contains a renal tubular cell and/or a mesangial cell.

8. The method according to claim 1, wherein the clonal embryonic kidney cell has an exogenous gene introduced therein.

9. The method according to claim 7, wherein the clonal embryonic kidney cell is HEK cell or M15 cell.

10. The method according to claim 7, wherein the cell group is free from iPS cell, ES cell, and/or a differentiation-induced cell thereof.

11. The method according to claim 7, wherein the co-culture is performed for 12 hours or more, and 36 hours or less.

12. The method according to claim 7, wherein the cell count ratio of the mesenchymal stem cell to the clonal embryonic kidney cell (mesenchymal stem cell:clonal embryonic kidney cell) is 1:10 to 10:1.

13. The method according to claim 7, wherein the clonal embryonic kidney cell has an exogenous gene introduced therein.

14. The method according to claim 7, wherein the mesenchymal stem cell, the vascular endothelial cell, and the clonal embryonic kidney cell are derived from a human or a mouse.

* * * * *

SEQUENCE LISTING

<160> NUMBER OF SEQ ID NOS: 56

<210> SEQ ID NO 1
<211> LENGTH: 22
<212> TYPE: DNA
<213> ORGANISM: artificial
<220> FEATURE:
<223> OTHER INFORMATION: primer

<400> SEQUENCE: 1
ggacatagtc tgcactgtcg at    22

```
<210> SEQ ID NO 2
<211> LENGTH: 21
<212> TYPE: DNA
<213> ORGANISM: artificial
<220> FEATURE:
<223> OTHER INFORMATION: primer

<400> SEQUENCE: 2
ggcaaatctg acaacaagac g                                              21

<210> SEQ ID NO 3
<211> LENGTH: 22
<212> TYPE: DNA
<213> ORGANISM: artificial
<220> FEATURE:
<223> OTHER INFORMATION: primer

<400> SEQUENCE: 3
gtacgagagc gataaccaca ca                                             22

<210> SEQ ID NO 4
<211> LENGTH: 22
<212> TYPE: DNA
<213> ORGANISM: artificial
<220> FEATURE:
<223> OTHER INFORMATION: primer

<400> SEQUENCE: 4
ggcttttcac ctgtatgagt cc                                             22

<210> SEQ ID NO 5
<211> LENGTH: 22
<212> TYPE: DNA
<213> ORGANISM: artificial
<220> FEATURE:
<223> OTHER INFORMATION: primer

<400> SEQUENCE: 5
aaaaccaaag aaaccaccac ct                                             22

<210> SEQ ID NO 6
<211> LENGTH: 22
<212> TYPE: DNA
<213> ORGANISM: artificial
<220> FEATURE:
<223> OTHER INFORMATION: primer

<400> SEQUENCE: 6
ggcatctttg gtctatttgc ag                                             22

<210> SEQ ID NO 7
<211> LENGTH: 22
<212> TYPE: DNA
<213> ORGANISM: artificial
<220> FEATURE:
<223> OTHER INFORMATION: primer

<400> SEQUENCE: 7
ctatccctgg ctacaccttc ac                                             22

<210> SEQ ID NO 8
<211> LENGTH: 22
<212> TYPE: DNA
<213> ORGANISM: artificial
<220> FEATURE:
<223> OTHER INFORMATION: primer
```

<400> SEQUENCE: 8
ctcggcatat cagtgagatc aa                                                22

<210> SEQ ID NO 9
<211> LENGTH: 22
<212> TYPE: DNA
<213> ORGANISM: artificial
<220> FEATURE:
<223> OTHER INFORMATION: primer

<400> SEQUENCE: 9
gctactaccg aatggaaaat gc                                                22

<210> SEQ ID NO 10
<211> LENGTH: 22
<212> TYPE: DNA
<213> ORGANISM: artificial
<220> FEATURE:
<223> OTHER INFORMATION: primer

<400> SEQUENCE: 10
agttctgttg ctgggagaag ac                                                22

<210> SEQ ID NO 11
<211> LENGTH: 22
<212> TYPE: DNA
<213> ORGANISM: artificial
<220> FEATURE:
<223> OTHER INFORMATION: primer

<400> SEQUENCE: 11
gagcaccttc acaagaatga aa                                                22

<210> SEQ ID NO 12
<211> LENGTH: 22
<212> TYPE: DNA
<213> ORGANISM: artificial
<220> FEATURE:
<223> OTHER INFORMATION: primer

<400> SEQUENCE: 12
attggagttc tcgttgttct cc                                                22

<210> SEQ ID NO 13
<211> LENGTH: 22
<212> TYPE: DNA
<213> ORGANISM: artificial
<220> FEATURE:
<223> OTHER INFORMATION: primer

<400> SEQUENCE: 13
tgcacaaaat caacaatgtg aa                                                22

<210> SEQ ID NO 14
<211> LENGTH: 22
<212> TYPE: DNA
<213> ORGANISM: artificial
<220> FEATURE:
<223> OTHER INFORMATION: primer

<400> SEQUENCE: 14
ttctcgtagt cctccatcag gt                                                22

<210> SEQ ID NO 15

```
<211> LENGTH: 22
<212> TYPE: DNA
<213> ORGANISM: artificial
<220> FEATURE:
<223> OTHER INFORMATION: primer

<400> SEQUENCE: 15
gtccttcaag aacccaaaac tg                                              22

<210> SEQ ID NO 16
<211> LENGTH: 22
<212> TYPE: DNA
<213> ORGANISM: artificial
<220> FEATURE:
<223> OTHER INFORMATION: primer

<400> SEQUENCE: 16
caatctggcc acagaaatca ta                                              22

<210> SEQ ID NO 17
<211> LENGTH: 22
<212> TYPE: DNA
<213> ORGANISM: artificial
<220> FEATURE:
<223> OTHER INFORMATION: primer

<400> SEQUENCE: 17
taaccctgct accctcatgt ct                                              22

<210> SEQ ID NO 18
<211> LENGTH: 22
<212> TYPE: DNA
<213> ORGANISM: artificial
<220> FEATURE:
<223> OTHER INFORMATION: primer

<400> SEQUENCE: 18
tccacagtga tgtctccata gg                                              22

<210> SEQ ID NO 19
<211> LENGTH: 22
<212> TYPE: DNA
<213> ORGANISM: artificial
<220> FEATURE:
<223> OTHER INFORMATION: primer

<400> SEQUENCE: 19
aggagctcac caatgagatg at                                              22

<210> SEQ ID NO 20
<211> LENGTH: 22
<212> TYPE: DNA
<213> ORGANISM: artificial
<220> FEATURE:
<223> OTHER INFORMATION: primer

<400> SEQUENCE: 20
tcctcgttct gataagcagt ca                                              22

<210> SEQ ID NO 21
<211> LENGTH: 24
<212> TYPE: DNA
<213> ORGANISM: artificial
<220> FEATURE:
<223> OTHER INFORMATION: primer

<400> SEQUENCE: 21
```

```
ccacccatgg caaattccat ggca                                          24

<210> SEQ ID NO 22
<211> LENGTH: 24
<212> TYPE: DNA
<213> ORGANISM: artificial
<220> FEATURE:
<223> OTHER INFORMATION: primer

<400> SEQUENCE: 22
tctagacggc aggtcaggtc cacc                                          24

<210> SEQ ID NO 23
<211> LENGTH: 22
<212> TYPE: DNA
<213> ORGANISM: artificial
<220> FEATURE:
<223> OTHER INFORMATION: primer

<400> SEQUENCE: 23
agaagggatg tctctttgac ca                                            22

<210> SEQ ID NO 24
<211> LENGTH: 22
<212> TYPE: DNA
<213> ORGANISM: artificial
<220> FEATURE:
<223> OTHER INFORMATION: primer

<400> SEQUENCE: 24
ctggtgggtt ctctccttat tg                                            22

<210> SEQ ID NO 25
<211> LENGTH: 22
<212> TYPE: DNA
<213> ORGANISM: artificial
<220> FEATURE:
<223> OTHER INFORMATION: primer

<400> SEQUENCE: 25
gaacttccag gacaaccaat tc                                            22

<210> SEQ ID NO 26
<211> LENGTH: 22
<212> TYPE: DNA
<213> ORGANISM: artificial
<220> FEATURE:
<223> OTHER INFORMATION: primer

<400> SEQUENCE: 26
cctttagttc cgaagtcagc tc                                            22

<210> SEQ ID NO 27
<211> LENGTH: 22
<212> TYPE: DNA
<213> ORGANISM: artificial
<220> FEATURE:
<223> OTHER INFORMATION: primer

<400> SEQUENCE: 27
gcccttcctt gagatgatac ac                                            22

<210> SEQ ID NO 28
<211> LENGTH: 22
<212> TYPE: DNA
```

```
<213> ORGANISM: artificial
<220> FEATURE:
<223> OTHER INFORMATION: primer

<400> SEQUENCE: 28
cagtgatggg atcagagtca aa                                              22

<210> SEQ ID NO 29
<211> LENGTH: 22
<212> TYPE: DNA
<213> ORGANISM: artificial
<220> FEATURE:
<223> OTHER INFORMATION: primer

<400> SEQUENCE: 29
ttagaggtca gcgtgtgtga ct                                              22

<210> SEQ ID NO 30
<211> LENGTH: 22
<212> TYPE: DNA
<213> ORGANISM: artificial
<220> FEATURE:
<223> OTHER INFORMATION: primer

<400> SEQUENCE: 30
ggagttcagg gagctcagac ta                                              22

<210> SEQ ID NO 31
<211> LENGTH: 22
<212> TYPE: DNA
<213> ORGANISM: artificial
<220> FEATURE:
<223> OTHER INFORMATION: primer

<400> SEQUENCE: 31
caaaccaatc gactttgaaa ca                                              22

<210> SEQ ID NO 32
<211> LENGTH: 22
<212> TYPE: DNA
<213> ORGANISM: artificial
<220> FEATURE:
<223> OTHER INFORMATION: primer

<400> SEQUENCE: 32
ggaagatcaa aagcaaatgg tc                                              22

<210> SEQ ID NO 33
<211> LENGTH: 22
<212> TYPE: DNA
<213> ORGANISM: artificial
<220> FEATURE:
<223> OTHER INFORMATION: primer

<400> SEQUENCE: 33
aatgaatgcc agtcttcacc tt                                              22

<210> SEQ ID NO 34
<211> LENGTH: 22
<212> TYPE: DNA
<213> ORGANISM: artificial
<220> FEATURE:
<223> OTHER INFORMATION: primer

<400> SEQUENCE: 34
agacctggtg acatcatctc ct                                              22
```

<210> SEQ ID NO 35
<211> LENGTH: 18
<212> TYPE: DNA
<213> ORGANISM: artificial
<220> FEATURE:
<223> OTHER INFORMATION: primer

<400> SEQUENCE: 35
ccagcttgaa tgcatgac                                                18

<210> SEQ ID NO 36
<211> LENGTH: 20
<212> TYPE: DNA
<213> ORGANISM: artificial
<220> FEATURE:
<223> OTHER INFORMATION: primer

<400> SEQUENCE: 36
cccaaacttt ttctgacaac                                              20

<210> SEQ ID NO 37
<211> LENGTH: 22
<212> TYPE: DNA
<213> ORGANISM: artificial
<220> FEATURE:
<223> OTHER INFORMATION: primer

<400> SEQUENCE: 37
gcttctgggc tctatctgaa aa                                           22

<210> SEQ ID NO 38
<211> LENGTH: 22
<212> TYPE: DNA
<213> ORGANISM: artificial
<220> FEATURE:
<223> OTHER INFORMATION: primer

<400> SEQUENCE: 38
gactagcagc tgcccattat ct                                           22

<210> SEQ ID NO 39
<211> LENGTH: 22
<212> TYPE: DNA
<213> ORGANISM: artificial
<220> FEATURE:
<223> OTHER INFORMATION: primer

<400> SEQUENCE: 39
cttctttcta cccccacaac ag                                           22

<210> SEQ ID NO 40
<211> LENGTH: 22
<212> TYPE: DNA
<213> ORGANISM: artificial
<220> FEATURE:
<223> OTHER INFORMATION: primer

<400> SEQUENCE: 40
ggagaaagct tcgtctcgat aa                                           22

<210> SEQ ID NO 41
<211> LENGTH: 22
<212> TYPE: DNA
<213> ORGANISM: artificial
<220> FEATURE:

<223> OTHER INFORMATION: primer

<400> SEQUENCE: 41
atttaacagc acattgcctc ct                                        22

<210> SEQ ID NO 42
<211> LENGTH: 22
<212> TYPE: DNA
<213> ORGANISM: artificial
<220> FEATURE:
<223> OTHER INFORMATION: primer

<400> SEQUENCE: 42
acagagatgt tcgaggtgg at                                         22

<210> SEQ ID NO 43
<211> LENGTH: 22
<212> TYPE: DNA
<213> ORGANISM: artificial
<220> FEATURE:
<223> OTHER INFORMATION: primer

<400> SEQUENCE: 43
cgtctccaga ccttggaaat ac                                        22

<210> SEQ ID NO 44
<211> LENGTH: 22
<212> TYPE: DNA
<213> ORGANISM: artificial
<220> FEATURE:
<223> OTHER INFORMATION: primer

<400> SEQUENCE: 44
gaggaacttg ggtagttgat gc                                        22

<210> SEQ ID NO 45
<211> LENGTH: 22
<212> TYPE: DNA
<213> ORGANISM: artificial
<220> FEATURE:
<223> OTHER INFORMATION: primer

<400> SEQUENCE: 45
gaagccttgg agaaaacaga ga                                        22

<210> SEQ ID NO 46
<211> LENGTH: 22
<212> TYPE: DNA
<213> ORGANISM: artificial
<220> FEATURE:
<223> OTHER INFORMATION: primer

<400> SEQUENCE: 46
ccattgtgta gttggtgtgc tt                                        22

<210> SEQ ID NO 47
<211> LENGTH: 22
<212> TYPE: DNA
<213> ORGANISM: artificial
<220> FEATURE:
<223> OTHER INFORMATION: primer

<400> SEQUENCE: 47
ggaagaagga tggctagaag ga                                        22

```
<210> SEQ ID NO 48
<211> LENGTH: 22
<212> TYPE: DNA
<213> ORGANISM: artificial
<220> FEATURE:
<223> OTHER INFORMATION: primer

<400> SEQUENCE: 48
ttcaccatcc tctgtggact ct                                             22

<210> SEQ ID NO 49
<211> LENGTH: 22
<212> TYPE: DNA
<213> ORGANISM: artificial
<220> FEATURE:
<223> OTHER INFORMATION: primer

<400> SEQUENCE: 49
ggtgctgaag gtaaatgtgt ca                                             22

<210> SEQ ID NO 50
<211> LENGTH: 22
<212> TYPE: DNA
<213> ORGANISM: artificial
<220> FEATURE:
<223> OTHER INFORMATION: primer

<400> SEQUENCE: 50
aggctttagc aaatgggttg ta                                             22

<210> SEQ ID NO 51
<211> LENGTH: 22
<212> TYPE: DNA
<213> ORGANISM: artificial
<220> FEATURE:
<223> OTHER INFORMATION: primer

<400> SEQUENCE: 51
tgatcgctct ctatgcaacc ta                                             22

<210> SEQ ID NO 52
<211> LENGTH: 22
<212> TYPE: DNA
<213> ORGANISM: artificial
<220> FEATURE:
<223> OTHER INFORMATION: primer

<400> SEQUENCE: 52
ccaagaagtg ccatatgttt ga                                             22

<210> SEQ ID NO 53
<211> LENGTH: 22
<212> TYPE: DNA
<213> ORGANISM: artificial
<220> FEATURE:
<223> OTHER INFORMATION: primer

<400> SEQUENCE: 53
gagaccagct actgcttcaa gg                                             22

<210> SEQ ID NO 54
<211> LENGTH: 22
<212> TYPE: DNA
<213> ORGANISM: artificial
<220> FEATURE:
<223> OTHER INFORMATION: primer
```

```
<400> SEQUENCE: 54
gacatggggt tgagtatgga gt                                              22

<210> SEQ ID NO 55
<211> LENGTH: 22
<212> TYPE: DNA
<213> ORGANISM: artificial
<220> FEATURE:
<223> OTHER INFORMATION: primer

<400> SEQUENCE: 55
tatgactcca ctcacggcaa at                                              22

<210> SEQ ID NO 56
<211> LENGTH: 22
<212> TYPE: DNA
<213> ORGANISM: artificial
<220> FEATURE:
<223> OTHER INFORMATION: primer

<400> SEQUENCE: 56
tgcttcacca ccttcttgat gt                                              22
```